United States Patent
Lee et al.

(10) Patent No.: US 12,324,819 B2
(45) Date of Patent: Jun. 10, 2025

(54) **COMPOSITION CONTAINING *ENTEROCOCCUS FAECALIS* AS ACTIVE INGREDIENT FOR PREVENTING OR TREATING OBESITY OR METABOLIC SYNDROMES INDUCED THEREBY**

(71) Applicant: DOCTOR TJ CO., LTD, Wonju-si (KR)

(72) Inventors: Jin Ho Lee, Seoul (KR); Sun Hong Kim, Wonju-si (KR)

(73) Assignee: DOCTOR TJ CO., LTD, Wonju-si (KR)

( * ) Notice: Subject to any disclaimer, the term of this patent is extended or adjusted under 35 U.S.C. 154(b) by 586 days.

(21) Appl. No.: 17/616,088

(22) PCT Filed: Oct. 21, 2020

(86) PCT No.: PCT/KR2020/014364
§ 371 (c)(1),
(2) Date: Dec. 2, 2021

(87) PCT Pub. No.: WO2021/080298
PCT Pub. Date: Apr. 29, 2021

(65) Prior Publication Data
US 2022/0313750 A1   Oct. 6, 2022

(30) Foreign Application Priority Data
Oct. 24, 2019   (KR) .................. 10-2019-0133242

(51) Int. Cl.
*A61K 35/744* (2015.01)
*A23L 33/135* (2016.01)
*A61P 3/04* (2006.01)

(52) U.S. Cl.
CPC .......... *A61K 35/744* (2013.01); *A23L 33/135* (2016.08); *A61P 3/04* (2018.01)

(58) Field of Classification Search
CPC ........ A61P 3/04; A61K 35/744; A23L 33/135
See application file for complete search history.

(56) References Cited

U.S. PATENT DOCUMENTS

| 11,564,955 B2 * | 1/2023 | Lee et al. ............. A61K 35/744 |
| 11,679,134 B2 * | 6/2023 | Kim et al. ........... A61K 35/744 |
| 2013/0089633 A1 | 4/2013 | Nakamura et al. |

FOREIGN PATENT DOCUMENTS

| JP | A 2019-535828 | 12/2019 |
| KR | 10-1508586 B1 | 4/2015 |

(Continued)

OTHER PUBLICATIONS

Joe et al. Depot-specific differences in adipogenic progenitor abundance and proliferative response to high-fat diet. Stem Cells, vol. 27: pp. 2563-2570. (Year: 2009).*

(Continued)

*Primary Examiner* — Louise W Humphrey
*Assistant Examiner* — Candice Lee Swift
(74) *Attorney, Agent, or Firm* — MH2 Technology Law Group, LLP (57) ABSTRACT

The present invention relates to a composition for prevention or treatment of obesity or obesity-induced metabolic syndrome containing *Enterococcus faecalis* as an active ingredient. Specifically, it has been confirmed that *Enterococcus faecalis* EF-2001 exhibits the effect of inhibiting adipogenesis in adipocytes, and thus the *Enterococcus faecalis*, a culture solution thereof, or killed bacteria thereof can be greatly usefully used for the prevention, improvement and treatment of obesity that occurs through adipogenesis in adipocytes or obesity-induced metabolic syndrome disease.

6 Claims, 2 Drawing Sheets

(56) References Cited

FOREIGN PATENT DOCUMENTS

| KR | 10-1800632 | 12/2017 |
| KR | 10-2018-0056972 A | 5/2018 |
| KR | 10-1996079 | 7/2019 |
| KR | 10-2019-0103829 A | 9/2019 |

OTHER PUBLICATIONS

WebMD; https://www.webmd.com/cholesterol-management/high-cholesterol-and-high-blood-pressure; accessed Nov. 15, 2024 (Year: 2023).*

Cleveland Clinic; https://my.clevelandclinic.org/health/diseases/21656-hyperlipidemia; accessed Nov. 15, 2024 (Year: 2022).*

Gu et al., Medicine and biology, vol. 151 No. 10, 2007 (Year: 2007).*

Nihon Berumu Co.; http://www.brm.co.jp/eng/brm.html; accessed Nov. 19, 2024 (Year: 2015).*

International Search Report dated Feb. 2, 2021 for International Patent Application No. PCT/KR2020/014364 (Authorized officer, Unknown), 6 pages.

Motonaga et al., "Effect of Enterococcus faecalis FK-23 on anti-obesity mice", Nippon Shokuhin Kagaku Kogaku Kaishi, 2009, vol. 56, No. 10, pp. 541-544.

* cited by examiner

COMPOSITION CONTAINING *ENTEROCOCCUS FAECALIS* AS ACTIVE INGREDIENT FOR PREVENTING OR TREATING OBESITY OR METABOLIC SYNDROMES INDUCED THEREBY

CROSS-REFERENCE TO RELATED APPLICATIONS

This application is a U.S. National Stage application of PCT/KR2020/014364 filed 21 Oct. 2020, which claims priority to Korean Application No. 10-2019-0133242 filed 24 Oct. 2019, the entire disclosures of which are hereby incorporated by reference in their entireties.

TECHNICAL FIELD

The present invention relates to a composition for prevention or treatment of obesity or obesity-induced metabolic syndrome containing *Enterococcus faecalis* as an active ingredient, more particularly to a composition for prevention, improvement or treatment of obesity or obesity-induced metabolic syndrome containing *Enterococcus faecalis*, a culture solution thereof, or killed bacteria thereof as an active ingredient.

BACKGROUND ART

Metabolic syndrome is a clustering phenomenon of abdominal obesity, impaired glucose tolerance, hypertension, and dyslipidemia. Among others, obesity is considered as the most basic cause of metabolic syndrome, and the obese population is increasing year by year. In the modern society, overeating, stress, and insomnia have been known to cause obesity. Gradually, interest in the cause of obesity and the demand for treatment of obesity are also increasing.

From the fact that obesity increases the incidence of various metabolic diseases and actual weight loss significantly decreases the incidence of these diseases, understanding of the proliferation of adipocytes containing a lot of fat and the substances secreted from adipocytes and elucidating the regulatory mechanisms thereof in vivo are considered to be the basis for the development of therapeutic agents for obesity and various diseases caused by obesity. Accordingly, studies on the regulation of adipocyte differentiation are being actively conducted.

For example, the current study trend is focused on searching for substances that can inhibit the metabolic process related to adipocyte differentiation as a method for preventing or treating obesity and lipid-related metabolic diseases. In other words, based on the mechanism of obesity, attempts are being made to treat obesity through adipocytes control. This is to reduce the amount of fat by inhibiting fat synthesis or promoting lipolysis and oxidation, and to decrease the number of adipocytes by inhibiting adipocyte differentiation. Substances that mediate or modulate these processes are emerging as targets for development.

Meanwhile, microorganisms belonging to the genus *Enterococcus* exist widely in nature and use carbohydrates aerobically. In general, it is known that bacteria such as microorganisms belonging to the genus *Enterococcus* prevent damage caused by pathogenic microorganisms by in vivo antagonism or secreted antibacterial substances. Among others, *Enterococcus faecalis* EF-2001 has been identified by screening the intestinal flora of a 2-year-old girl. *Enterococcus faecalis* EF-2001 killed bacteria are those obtained by killing the *Enterococcus faecalis* EF-2001 through a heat treatment and recovering the bacterial components.

According to studies reported on the physiological activity of *Enterococcus faecalis* EF-2001, it has been reported that the dextran sulfate sodium (DSS) relieving effect is observed in mice ingested *Enterococcus faecalis* EF-2001 in the case of mice suffering from DSS-induced colitis and the proliferation of transplanted sarcoma cancer cells (Sarcoma-180) is reduced and NK cells are activated (Tadano et al., J. Japan Mibyou System association, 2011). With regard to the inhibition of harmful bacteria and intestinal function, *Enterococcus faecalis* EF-2001 inhibits the activity of *Candida albican*, the cause of white fur of tongue, to improve the symptoms and exhibit preventive effects (Ishijima et al., Med. Mycol. J, 2014), and it has been disclosed that *Enterococcus faecalis* EF-2001 has the efficacy of rapidly proliferating beneficial bacteria and inhibiting harmful bacteria in mice administered with antibiotics compared to the intestinal control group (Sirnohashi et al., Medicine and biology, 2002). The various physiological activities of *Enterococcus faecalis* EF-2001 are not affected by heat and pH because of the characteristics of killed bacteria, and thus *Enterococcus faecalis* EF-2001 has an advantage of being processed into various forms of preparations (Kan, Food industry, 2001). The content of *Enterococcus faecalis* EF-2001 is 7.5 trillion per gram, and thus a large number of lactic acid bacteria can be ingested with a small amount.

Korean Patent No. 10-1800632 discloses a pharmaceutical composition, a food composition and a food additive for prevention, improvement or treatment of muscle loss, muscle weakness and muscle atrophy, which contain *Enterococcus faecalis*, a culture solution thereof, or killed bacteria thereof as an active ingredient. Korean Patent Laid-Open No. 10-1996079 discloses a composition for prevention or treatment of hair loss containing *Enterococcus faecalis* as an active ingredient. However, the use of *Enterococcus faecalis* EF-2001 for the prevention, improvement or treatment of obesity or obesity-induced metabolic syndrome based on the prevention of obesity through inhibition of adipogenesis has not been revealed.

Hence, the present inventors have made efforts to develop a material having fewer side effects and excellent treatment effects for obesity and obesity-induced metabolic syndrome, as a result, confirmed that *Enterococcus faecalis* EF-2001 has the effect of inhibiting adipogenesis in adipocytes, and revealed that *Enterococcus faecalis* of the present invention, a culture solution thereof, or killed bacteria thereof can be used as a composition or functional material for the prevention, improvement or treatment of obesity that occurs through adipogenesis in adipocytes or obesity-induced metabolic syndrome to complete the present invention.

SUMMARY OF INVENTION

Technical Problem

An object of the present invention is to provide a composition for prevention, improvement or treatment of obesity or obesity-induced metabolic syndrome containing *Enterococcus faecalis*, which has adipogenesis inhibitory activity and can be thus greatly usefully used for the prevention, improvement and treatment of obesity that occurs through adipogenesis in adipocytes or obesity-induced metabolic syndrome disease, a culture solution thereof, or killed bacteria thereof as an active ingredient.

Another object of the present invention is to provide a method for preventing or treating obesity or obesity-induced metabolic syndrome, which includes a step of administering a pharmaceutically effective amount of *Enterococcus faecalis*, a culture solution thereof, or killed bacteria thereof to a subject.

In addition, an object of the present invention is to provide the use of *Enterococcus faecalis*, a culture solution thereof, or killed bacteria thereof to be used as a composition for prevention or treatment of obesity or obesity-induced metabolic syndrome.

Solution to Problem

The objects of the present invention are achieved by providing a pharmaceutical composition for prevention or treatment of obesity or obesity-induced metabolic syndrome containing any one or more selected from the group consisting of *Enterococcus faecalis*, a culture solution thereof, and killed bacteria thereof as an active ingredient; a method for preventing or treating obesity or obesity-induced metabolic syndrome, which includes a step of administering a pharmaceutically effective amount of any one or more selected from the group consisting of *Enterococcus faecalis*, a culture solution thereof, and killed bacteria thereof to a subject; and the use of any one or more selected from the group consisting of *Enterococcus faecalis*, a culture solution thereof, and killed bacteria thereof to be used as a pharmaceutical composition for prevention or treatment of obesity or obesity-induced metabolic syndrome.

The objects of the present invention are achieved by providing a health functional food composition for improvement of obesity or obesity-induced metabolic syndrome containing any one or more selected from the group consisting of *Enterococcus faecalis*, a culture solution thereof, and killed bacteria thereof as an active ingredient; and the use of any one or more selected from the group consisting of *Enterococcus faecalis*, a culture solution thereof, and killed bacteria thereof to be used as a health functional food composition for improvement of obesity or obesity-induced metabolic syndrome.

The objects of the present invention are achieved by providing a food additive for improvement of obesity or obesity-induced metabolic syndrome containing any one or more selected from the group consisting of *Enterococcus faecalis*, a culture solution thereof, and killed bacteria thereof as an active ingredient; and the use of any one or more selected from the group consisting of *Enterococcus faecalis*, a culture solution thereof, and killed bacteria thereof to be used as a food additive for improvement of obesity or obesity-induced metabolic syndrome.

The objects of the present invention are achieved by providing an external preparation for improvement of obesity or obesity-induced metabolic syndrome containing any one or more selected from the group consisting of *Enterococcus faecalis*, a culture solution thereof, and killed bacteria thereof as an active ingredient; and the use of any one or more selected from the group consisting of *Enterococcus faecalis*, a culture solution thereof, and killed bacteria thereof to be used as an external preparation for improvement of obesity or obesity-induced metabolic syndrome.

In addition, the objects of the present invention are achieved by providing a cosmetic for improvement of obesity or obesity-induced metabolic syndrome containing any one or more selected from the group consisting of *Enterococcus faecalis*, a culture solution thereof, and killed bacteria thereof as an active ingredient; and the use of any one or more selected from the group consisting of *Enterococcus faecalis*, a culture solution thereof, and killed bacteria thereof to be used as a cosmetic for improvement of obesity or obesity-induced metabolic syndrome.

Advantageous Effects of Invention

In the present invention, it has been confirmed that *Enterococcus faecalis* EF-2001 exhibits the effect of inhibiting adipogenesis in adipocytes, and thus the *Enterococcus faecalis*, a culture solution thereof, or killed bacteria thereof can be greatly usefully used for the prevention, improvement and treatment of obesity that occurs through adipogenesis in adipocytes or obesity-induced metabolic syndrome disease.

DESCRIPTION OF EMBODIMENTS

Hereinafter, preferred embodiments of the present invention and the physical properties of each component will be described in detail, but it is intended to explain the invention in detail enough that a person of ordinary skill in the art to which the present invention pertains can easily carry out the invention, and it does not mean that the technical spirit and scope of the present invention is limited by this.

As used herein, the term "adipocyte" refers to an adipocyte differentiated from a preadipocyte and a cell that produces fat in vivo. As used herein, the term "obesity" refers to providing a cause of disease or illness due to excessive adipogenesis.

In the present invention, "metabolic syndrome" includes, for example, a combination of symptoms appearing as a cluster of abdominal adipogenesis, impaired glucose tolerance, hypertension, and dyslipidemia.

Preferably, the obesity disease to be treated, improved or prevented by the present invention is abdominal adipogenesis, impaired glucose tolerance, hypertension, and dyslipidemia belonging to the metabolic syndrome.

Metabolic syndrome includes a combination of symptoms appearing as a cluster of abdominal adipogenesis, impaired glucose tolerance, hypertension, and dyslipidemia. *Enterococcus faecalis*, which highly efficiently inhibits adipogenesis in adipocytes, is greatly effective in the treatment of metabolic syndrome diseases.

As used herein, the term "prevention" refers to inhibiting the occurrence of disease or illness in an animal that has never been diagnosed as possessing disease or illness but is prone to such disease or illness. As used herein, the term "treatment" refers to (i) inhibition of the development of disease or illness; (ii) alleviation of disease or illness; and (iii) elimination of disease or illness.

The present invention provides a pharmaceutical composition for prevention or treatment of obesity or obesity-induced metabolic syndrome containing any one or more selected from the group consisting of *Enterococcus faecalis*, a culture solution thereof, and killed bacteria thereof as an active ingredient; a method for preventing or treating obesity or obesity-induced metabolic syndrome, which includes a step of administering a pharmaceutically effective amount of any one or more selected from the group consisting of *Enterococcus faecalis*, a culture solution thereof, and killed bacteria thereof to a subject; and the use of any one or more selected from the group consisting of *Enterococcus faecalis*, a culture solution thereof, and killed bacteria thereof to be used as a pharmaceutical composition for prevention or treatment of obesity or obesity-induced metabolic syndrome.

In the present invention, the *Enterococcus faecalis* is preferably *Enterococcus faecalis* EF-2001, but is not limited thereto.

In the present invention, any one of commercially available one or one prepared by a known killed bacteria preparation method may be used as the *Enterococcus faecalis*, a culture solution thereof, or killed bacteria thereof, and the *Enterococcus faecalis*, a culture solution thereof, or killed bacteria thereof do not exhibit toxicity and are harmless to the human body.

The culture solution refers to a culture solution containing *Enterococcus faecalis* cultured in a culture medium, a concentrated culture solution, a dried product of a culture solution, a culture filtrate, a concentrated culture filtrate, or a dried product of a culture filtrate, and may be a culture solution containing the strain or a culture solution from which the strain has been removed after culture.

The killed bacteria may be prepared by subjecting the corresponding live bacteria to a heat treatment or treating the corresponding live bacteria with formalin or other disinfectants, and substantially killed bacteria can also be used. The killed bacteria include a killed bacteria suspension obtained by washing, centrifuging, repeatedly washing and dehydrating if necessary, and then suspending a strain obtained through culture by a conventional method in distilled water, physiological saline or the like and heating the suspension, for example, at 80° C. to 115° C. for 30 minutes to 3 seconds or a dried product thereof; or a killed bacteria suspension obtained by irradiating the killed bacteria suspension with a gamma ray or a neutron beam or a dried product thereof. The drying means for the killed bacteria suspension is not particularly limited as long as it is a known drying means, and spray drying, freeze drying, and the like may be an example. In some cases, enzyme treatment, surfactant treatment, grinding/pulverization treatment may be performed before and after sterilization treatment by heating or the like or before and after drying treatment. Those obtained by such treatments are also included in the killed bacteria of the present invention. In addition, the killed bacteria may be prepared in the following method, but are not limited thereto:

1) a step of subjecting *Enterococcus faecalis* to starter culture and then to main culture at a pH of 4.0 to 9.0 and a temperature of 15° C. to 45° C., more preferably at a pH of 5.0 to 8.0 and a temperature of 20° C. to 40° C.; and 2) a step of subjecting the *Enterococcus faecalis* subjected to main culture in step 1) to a heat treatment at a temperature of 60° C. to 140° C. for 1 to 40 minutes, more preferably at a temperature of 70° C. to 130° C. for 5 to 30 minutes and then drying and powdering the *Enterococcus faecalis*.

In the present invention, the obesity is induced by differentiation and proliferation of adipocytes, and metabolic syndrome is induced by such obesity. More specifically, the metabolic syndrome is one or more selected from the group consisting of abdominal adipogenesis, impaired glucose tolerance, hypertension, and dyslipidemia.

In a specific embodiment of the present invention, the present inventors have confirmed that *Enterococcus faecalis* EF-2001 exhibits the effect of inhibiting adipogenesis in adipocytes, and thus the *Enterococcus faecalis* can be greatly usefully used as an active ingredient of a pharmaceutical composition for prevention, improvement and treatment of obesity that occurs through adipogenesis in adipocytes or obesity-induced metabolic syndrome disease.

The composition of the present invention may contain the strain as an active ingredient at a content of $10^6$ to $10^{13}$ cfu/g, a culture having the equal number of live bacteria, or killed bacteria, with respect to the total weight of the composition. The composition may also be prepared as a composition of a conventional formulation by selecting one or two or more pharmaceutically acceptable conventional carriers or one or two or more additives and mixing these with an effective amount of the *Enterococcus faecalis* of the present invention, a culture solution thereof, or killed bacteria thereof, which is the main ingredient.

As the carriers, one or two or more of diluents, lubricants, binders, disintegrants, sweeteners, stabilizers, and preservatives may be selected and used. As the additives, one or two or more of fragrances, vitamins, and antioxidants may be selected and used.

In the present invention, all pharmaceutically acceptable ones may be used as the carriers and additives. Specifically, lactose monohydrate, trehalose, cornstarch, soybean oil, microcrystalline cellulose or D-mannitol is preferable as the diluent, magnesium stearate or talc is preferable as the lubricant, and the binder is preferably selected from polyvinylpyrrolidone (PVP) or hydroxypropylcellulose (HPC). The disintegrant is preferably selected from carboxymethylcellulose calcium (Ca-CMC), sodium starch glycolate, polacrilin potassium or cross-linked polyvinylpyrrolidone, the sweetener is preferably selected from sucrose, fructose, sorbitol or aspartame, the stabilizer is preferably selected from carboxymethylcellulose sodium (Na-CMC), beta-cyclodextrin, white bee's wax or xanthan gum, and the preservative is preferably selected from methyl p-hydroxy benzoate (methylparaben), propyl p-hydroxybenzoate (propylparaben), or potassium sorbate, but not limited thereto.

The pharmaceutical composition of the present invention may be administered to a patient as a single dose, and may be administered by a fractionated treatment protocol in which multiple doses are administered for a long period of time. As used herein, the term 'pharmaceutically effective amount' refers to an amount in which a response greater than that of the negative control group is exhibited, preferably refers to an amount sufficient to prevent or treat an inflammatory disease. The pharmaceutically effective amount may be appropriately changed depending on various factors such as the disease and its severity, the age, weight, health status, and sex of patient, the administration route, and the treatment period.

The composition of the present invention may be formulated together with a pharmaceutically acceptable carrier in various ways depending on the route of administration by methods known in the art. As used herein, the term "pharmaceutically acceptable" refers to a non-toxic composition that is physiologically acceptable, does not inhibit the action of the active ingredient when administered to humans, and usually does not cause allergic reactions such as gastrointestinal disorders and dizziness or reactions similar to the allergic reactions. The composition of the present invention may be formulated together with the pharmaceutically acceptable carrier in various ways depending on the route of administration by methods known in the art. The composition of the present invention may be administered orally or parenterally, but the route of administration is not limited thereto.

The present invention also provides a health functional food composition for improvement of obesity or obesity-induced metabolic syndrome containing *Enterococcus faecalis*, a culture solution thereof, or killed bacteria thereof as an active ingredient; and the use of *Enterococcus faecalis*, a culture solution thereof, or killed bacteria thereof to be used as a health functional food composition for improvement of obesity or obesity-induced metabolic syndrome.

The present invention also provides a food additive for improvement of obesity or obesity-induced metabolic syndrome containing *Enterococcus faecalis*, a culture solution thereof, or killed bacteria thereof as an active ingredient; and the use of *Enterococcus faecalis*, a culture solution thereof, or killed bacteria thereof to be used as a food additive for improvement of obesity or obesity-induced metabolic syndrome.

In the present invention, the *Enterococcus faecalis* is preferably *Enterococcus faecalis* EF-2001, but is not limited thereto.

The *Enterococcus faecalis*, the method for obtaining a culture solution thereof and killed bacteria thereof, and the type of obesity or obesity-induced metabolic syndrome are the same as those described in the pharmaceutical composition for improvement or treatment of obesity or obesity-induced metabolic syndrome containing the *Enterococcus faecalis*, a culture solution thereof, or killed bacteria thereof as an active ingredient, thus the specific description thereof refers to the above contents, and only the specific configuration of the health functional food will be described below.

Meanwhile, the present inventors have confirmed that *Enterococcus faecalis* EF-2001 exhibits the effect of inhibiting adipogenesis in adipocytes, and thus the *Enterococcus faecalis* can be greatly usefully used as an active ingredient of a health functional food composition or a food additive for prevention or improvement of obesity that occurs through adipogenesis in adipocytes or obesity-induced metabolic syndrome.

There is no particular limitation on the kind of food to which *Enterococcus faecalis* of the present invention is added. Examples of the food include drinks, meat, sausage, bread, biscuits, rice cake, chocolate, candy, snacks, confectionery, pizza, ramen, other noodles, gum, dairy products including ice cream, various soups, beverages, alcoholic beverages and vitamin complexes, and the food includes all health foods in a conventional sense.

The amount of *Enterococcus faecalis* according to the present invention mixed may be appropriately determined depending on the purpose of use (for prevention or improvement). In general, the *Enterococcus faecalis* may be added to the health food at 0.001% to 50% by weight of the total food weight. However, in the case of long-term intake for the purpose of health and hygiene or health control, the amount may be less than or equal to the above range, and the active ingredient does not have any problem in terms of safety and thus may be used in an amount exceeding the above range.

The health functional beverage composition of the present invention is only required to contain the *Enterococcus faecalis* as an essential ingredient at the prescribed ratio, and other ingredients are not particularly limited, and the health functional beverage composition may contain various flavoring agents or natural carbohydrates as an additional component like a conventional beverage. Examples of the natural carbohydrates include conventional sugars such as monosaccharides, for example, glucose and fructose; disaccharides, for example, maltose and sucrose; and polysaccharides, for example, dextrin and cyclodextrin, and sugar alcohols such as xylitol, sorbitol and erythritol. As flavoring agents other than those described above, natural flavoring agents (thaumatin, stevia extract (for example, rebaudioside A and glycyrrhizin) and synthetic flavoring agents (saccharin and aspartame) may be advantageously used.

In addition to the above, the food or food additive of the present invention may contain various nutrients, vitamins, minerals (electrolytes), flavor-enhancing agents such as synthetic and natural flavor-enhancing agents, colorants and thickeners (cheese, chocolate, and the like), pectic acid and its salts, alginic acid and its salts, organic acids, protective colloidal thickeners, pH adjusters, stabilizers, preservatives, glycerin, alcohols, carbonating agents used in carbonated beverages, and the like. In addition to these, *Enterococcus faecalis* of the present invention may contain natural fruit juice and pulp for the production of fruit juice beverages and vegetable beverages. These ingredients may be used independently or in combination. The proportion of these additives is not so critical, but is generally selected in the range of 0 to about 20 parts by weight per 100 parts by weight of *Enterococcus faecalis* of the present invention.

The present invention also provides an external preparation for improvement of obesity or obesity-induced metabolic syndrome containing *Enterococcus faecalis*, a culture solution thereof, or killed bacteria thereof as an active ingredient; and the use of *Enterococcus faecalis*, a culture solution thereof, or killed bacteria thereof to be used as an external preparation for improvement of obesity or obesity-induced metabolic syndrome.

In addition, the present invention provides a cosmetic for improvement of obesity or obesity-induced metabolic syndrome containing *Enterococcus faecalis*, a culture solution thereof, or killed bacteria thereof as an active ingredient; and the use of *Enterococcus faecalis*, a culture solution thereof, or killed bacteria thereof to be used as a cosmetic for improvement of obesity or obesity-induced metabolic syndrome.

In the present invention, the *Enterococcus faecalis* is preferably *Enterococcus faecalis* EF-2001, but is not limited thereto.

The *Enterococcus faecalis*, the method for obtaining a culture solution thereof and killed bacteria thereof, and the type of obesity or obesity-induced metabolic syndrome are the same as those described in the pharmaceutical composition for improvement or treatment of obesity or obesity-induced metabolic syndrome containing the *Enterococcus faecalis*, a culture solution thereof, or killed bacteria thereof as an active ingredient, thus the specific description thereof refers to the above contents, and only the specific configurations of the external preparation and cosmetic will be described below.

Meanwhile, the present inventors have confirmed that *Enterococcus faecalis* EF-2001 exhibits the effect of inhibiting adipogenesis in adipocytes, and thus the *Enterococcus faecalis* can be greatly usefully used as an active ingredient of an external preparation or a cosmetic for improvement of obesity that occurs through adipogenesis in adipocytes or obesity-induced metabolic syndrome.

The ingredients contained in the external application or cosmetic composition of the present invention may include ingredients commonly used in external preparations or cosmetic compositions in addition to the active ingredient, and include, for example, conventional adjuvants such as antioxidants, stabilizers, solubilizers, vitamins, pigments and fragrances, and carriers.

In order to formulate the active ingredient of the present invention into a preparation, the active ingredient may be easily formulated into a preparation by a conventional method, and surfactants, excipients, colorants, fragrances, preservatives, stabilizers, buffers, suspending agents, and other commercially available adjuvants may be appropriately used.

The composition of the present invention may be prepared in any formulation conventionally prepared in the art, and may be formulated into, for example, a solution, a suspension, an emulsion, paste, gel, cream, lotion, powder, soap, surfactant-containing cleansing oil, powder foundation, emulsion foundation, wax foundation, pack, massage cream and spray, but the formulation is not limited thereto. More specifically, the composition of the present invention may be prepared in a formulation of softening lotion, nutrient lotion, nourishing cream, massage cream, essence, eye cream, cleansing cream, cleansing foam, cleansing water, pack, spray or powder.

When the formulation of the present invention is paste, cream, or gel, animal oil, vegetable oil, wax, paraffin, starch, tragacanth, cellulose derivatives, polyethylene glycol, silicone, bentonite, silica, talc or zinc oxide may be used as a carrier component.

When the formulation of the present invention is a solution or an emulsion, a solvent, a solubilizer or an emulsifier is used as a carrier component, and examples thereof include water, ethanol, isopropanol, ethyl carbonate, ethyl acetate, benzyl alcohol, benzyl benzoate, propylene glycol, 1,3-butyl glycol oil, glycerol aliphatic esters, polyethylene glycol or fatty acid esters of sorbitan.

When the formulation of the present invention is a suspension, a liquid diluent such as water, ethanol or propylene glycol, suspending agents such as ethoxylated isostearyl alcohol, polyoxyethylene sorbitol ester, and polyoxyethylene sorbitan ester, microcrystalline cellulose, aluminum metahydroxide, bentonite, agar, or tragacanth may be used as a carrier component.

When the formulation of the present invention is powder or spray, lactose, talc, silica, aluminum hydroxide, calcium silicate or polyamide powder may be used as a carrier component. In particular, in the case of spray, the formulation may additionally contain a propellant such as chlorofluorohydrocarbon, propane/butane or dimethyl ether.

EXAMPLES

Hereinafter, the present invention will be described in detail with reference to Examples, Experimental Examples and Preparation Examples.

However, the following Examples, Experimental Examples and Preparation Examples are merely illustrative of the present invention, and the contents of the present invention are not limited by the following Examples, Experimental Examples and Preparation Examples.

<Example 1> Culture of *Enterococcus faecalis* EF-2001

*Enterococcus faecalis* EF-200 live bacteria (Nihon BERM Co. Ltd, Japan) were cultured aerobically or anaerobically in the medium used for general lactic acid bacteria culture as preculture, and then cultured for 1 to 3 days while maintaining the pH at 5.0 to 8.0 and the temperature at 20° C. to 40° C. as main culture so that the number of bacteria reached $7.5 \times 10^{12}$ cfu/g or more based on the dry weight (DW) and killed by heat treatment.

<Experimental Example 1> Cell Culture

3T3-L1 (mouse embryonic fibroblast cell line) preadipocytes were purchased from ATCC (American type culture collection), and cultured in DMEM medium (Dulbecco's modified Eagle's medium, WelGene Biopharmaceuticals, Daegu, Korea) supplemented with 10% BCS (bovine calf serum, WelGene Biopharmaceuticals, Daegu, Korea) and antibiotics (penicillin/streptomycin 100 units/ml, Bioshop, Burlington, Ontario, Canada) in a cell incubator under conditions of 37° C. and 5% $CO_2$.

<Experimental Example 2> Evaluation of Cytotoxicity of *Enterococcus faecalis* EF-2001

The cytotoxicity of *Enterococcus faecalis* EF-2001 was evaluated using MTT assay.

Specifically, the medium was removed from the 100 $cm^2$ culture plate in which 3T3-L1 preadipocytes were cultured by the method disclosed in <Experimental Example 1>, and the 3T3-L1 preadipocytes were washed with CMF-PBS (calcium magnesium free-phosphate buffered saline, pH 7.2) and then treated with 0.25% trypsin/EDTA to detach the cells from the culture plate, and the cells were neutralized with a cell culture medium and centrifuged at 1500 rpm for 5 minutes. After the culture medium was added to the pellet of the remaining cells, a single cell suspension was prepared by repeated suction with a sterile pipette. Thereafter, trypan blue was mixed with the cell suspension at a ratio of 9:1 by weight, and the cells were quantified using a hemocytometer on an optical microscope. The quantified 3T3-L1 preadipocytes were seeded in a 24-well plate at $5 \times 10^4$ cells/well. The cells were cultured in an incubator at 37° C. and 5% $CO_2$, and then differentiation inducing agents (IBMX, dexamethasone, Insulin) were added to induce differentiation of adipocytes when the cell concentration was 100% in the plate. *Enterococcus faecalis* EF-2001 cultured in <Example 1> was added thereto at concentrations of 0, 25, 100, and 250 μg/ml, respectively, and the cells were cultured for 48 hours to induce differentiation of adipocytes. Thereafter, 50 μl of 5 mg/ml MTT solution was added for cell viability, and the cells were incubated at 37° C. for 2 hours. The obtained formazan crystals were lysed in 150 μl of DMSO and transferred to a 96-well plate, and the absorbance was measured at 590 nm using a Victor™X3 multilabel reader (Perkin Elmer, Waltham, MA, USA).

Figure 1:
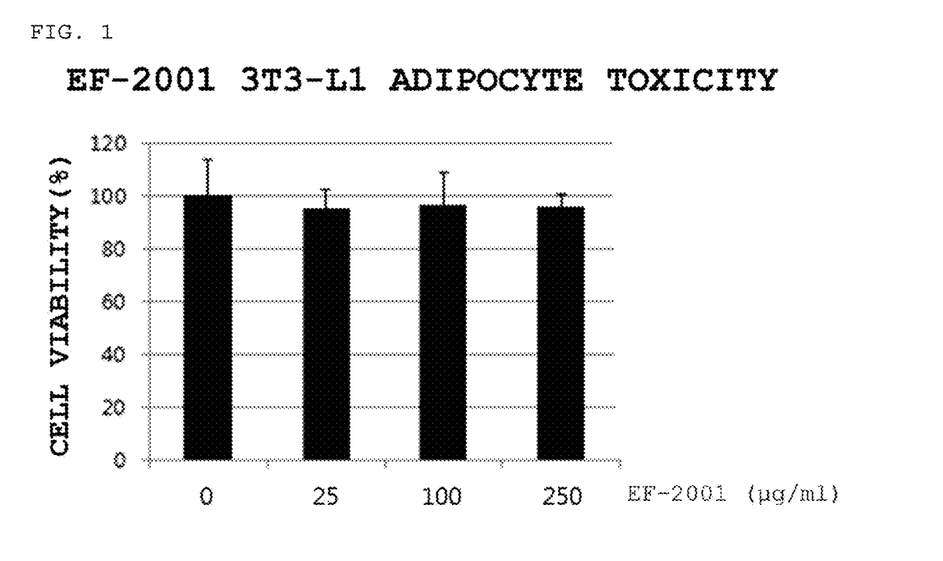
FIG. 1 illustrates the results of measuring the cytotoxicity of *Enterococcus faecalis* EF-2001.

As a result, as illustrated in FIG. 1, when the cell viability in the case of not adding *Enterococcus faecalis* EF-2001 is determined as 100%, it has been confirmed that the group to which *Enterococcus faecalis* EF-2001 was added has a cell viability similar to that in the group to which *Enterococcus faecalis* EF-2001 was not added.

From the results, it can be seen that *Enterococcus faecalis* EF-2001 of the present invention does not exhibit toxicity to adipocytes.

<Experimental Example 3> Confirmation of Effect of Inhibiting Adipogenesis in Adipocytes by *Enterococcus faecalis* EF-2001

To investigate the effect of *Enterococcus faecalis* EF-2001 on adipogenesis in adipocytes, 3T3-L1 preadipocytes were treated with *Enterococcus faecalis* EF-2001, differentiation of the adipocytes was induced, and then adipogenesis was examined using Oil Red O lipid assay.

Specifically, 3T3-L1 preadipocytes cultured in <Experimental Example 1> were treated with *Enterococcus faecalis* EF-2001 cultured in <Example 1> at concentrations of 0, 25, 100, and 250 μg/ml and differentiation of adipocytes was induced in the same manner as in <Experimental Example 2>. Thereafter, the medium was replaced with a fresh 10% FBS serum medium containing insulin at 10 μg/ml, the adipogenesis stimulation was maintained for 48 hours, and the stabilization period was maintained again for 48 hours using fresh medium containing serum. Thereafter, the medium was removed, the cells were washed with cold PBS (Gibco, Grand Island, NY, USA), and the cells in each well were then treated with 10% formalin (formalin, Junsei Chemical, Tokyo, Japan) and fixed at room temperature for 1 hour.

Figure 3:
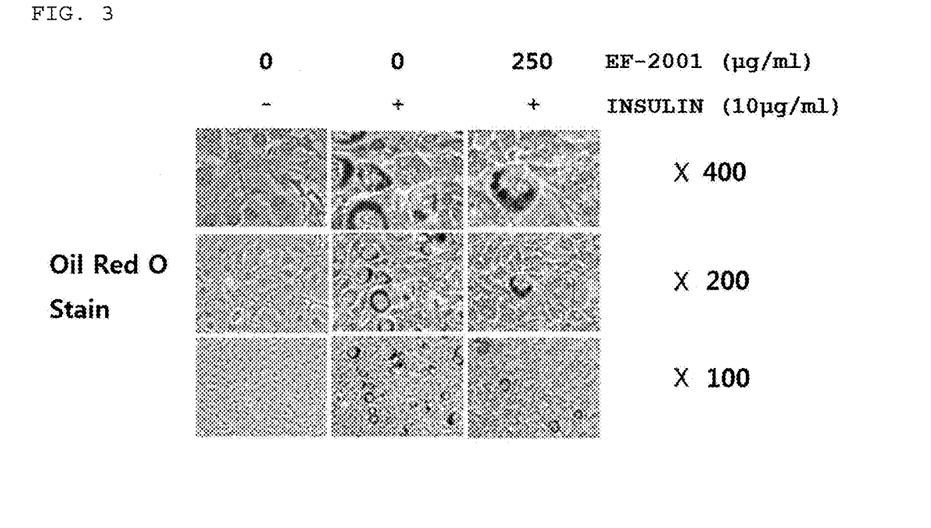
FIG. 3 is the visually confirmed effect of inhibiting adipogenesis in adipocytes by *Enterococcus faecalis* EF-2001 at various concentrations.

Thereafter, the cells in each well were treated with 60% isopropanol for 5 minutes, treated with Oil Red O stain solution, and stained for 10 minutes. After washing with distilled water was performed, the images of only the cells treated with *Enterococcus faecalis* EF-2001 at concentrations of 0 and 250 μg/ml were taken at 100-fold, 200-fold, and 400-fold magnifications using an optical microscope (FIG. 3). Thereafter, the cells in each well treated with *Enterococcus faecalis* EF-2001 at concentrations of 0, 25, 100, and 250 μg/ml were treated with 100% isopropanol, then obtained for every concentration, and transferred to a 96-well plate, and then the wavelength was measured at 490 nm using a microplate reader.

Figure 2:
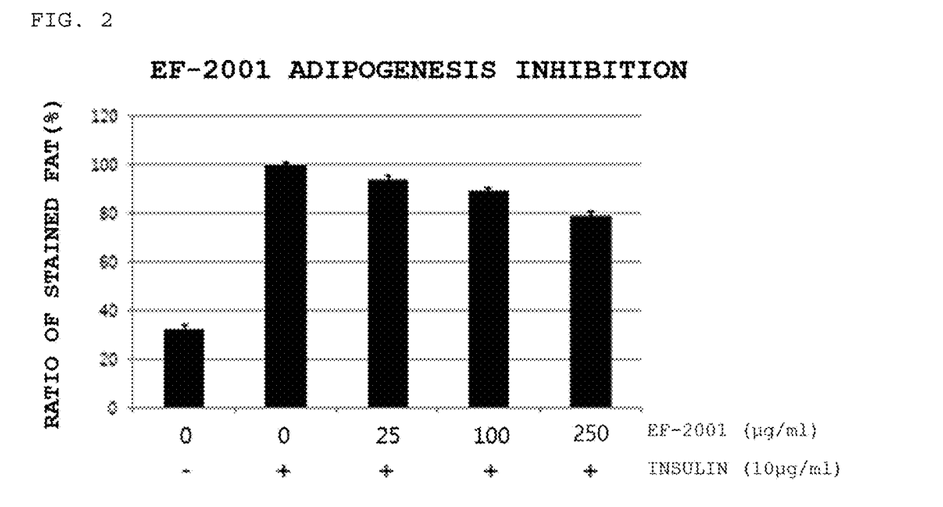
FIG. 2 illustrates the effect of inhibiting adipogenesis in adipocytes by *Enterococcus faecalis* EF-2001 at various concentrations.

As a result, as illustrated in FIG. 2, it has been confirmed that adipogenesis in adipocytes is significantly increased in the case of treating the cells with only insulin after differentiation of adipocytes has proceeded. On the other hand, it has been confirmed that adipogenesis in adipocytes is significantly decreased in the case of treating the cells with *Enterococcus faecalis* EF-2001 and insulin. It has also been confirmed that adipogenesis in adipocytes is decreased in a concentration-dependent manner as the concentration of *Enterococcus faecalis* EF-2001 increases.

As illustrated in FIG. 3, it has been confirmed through observation under a microscope that the size and number of fat-formed droplets are significantly increased in the case of treating the cells with only insulin after differentiation of adipocytes has proceeded. On the other hand, it has been confirmed that the number of fat-formed droplets is significantly decreased in the case of treating the cells with *Enterococcus faecalis* EF-2001 and insulin. It has also been confirmed that the number of fat-formed droplets is decreased in a concentration-dependent manner as the concentration of *Enterococcus faecalis* EF-2001 increases.

From the results above, it can be seen that *Enterococcus faecalis* EF-2001 of the present invention exhibits an effect of inhibiting adipogenesis in adipocytes in a concentration-dependent manner.

Consequently, it has been confirmed through the results above that *Enterococcus faecalis* EF-2001 according to the present invention exhibits the effect of inhibiting adipogenesis in adipocytes, and thus the *Enterococcus faecalis*, a culture solution thereof, or killed bacteria thereof can be greatly usefully used for the early prevention, improvement and treatment of obesity or obesity-induced metabolic syndrome disease by reducing the possibility of obesity that occurs through adipogenesis in adipocytes.

Preparation Examples for the composition of the present invention are exemplified below.

<Preparation Example 1> Preparation of Pharmaceutical Preparation Containing *Enterococcus faecalis* EF-2001 of Present Invention as Active Ingredient <1-1> Preparation of Powder
  *Enterococcus faecalis* EF-2001 of present invention: 10 mg
  Lactose: 1 g
  The ingredients were mixed together and filled in an airtight pouch to prepare a powder.
<1-2> Preparation of Tablet
  *Enterococcus faecalis* EF-2001 of present invention: 0.1 mg
  Cornstarch: 100 mg
  Lactose: 100 mg
  Magnesium stearate: 2 mg
  The ingredients were mixed together, and then tablets were prepared by tableting the mixture according to a conventional method for preparing tablets.
<1-3> Preparation of Capsule
  *Enterococcus faecalis* EF-2001 of present invention: 0.1 mg
  Cornstarch: 100 mg
  Lactose: 100 mg
  Magnesium stearate: 2 mg
  The ingredients were mixed together, and then capsules were prepared by filling the mixture in gelatin capsules according to a conventional method for preparing capsules.
<1-4> Preparation of Pill
  *Enterococcus faecalis* EF-2001 of present invention: 1 mg
  Lactose: 1.5 g
  Glycerin: 1 g
  Xylitol: 0.5 g
  The ingredients were mixed together, and then pills were prepared so as to be 4 g per one pill according to a conventional method.
<1-5> Preparation of Granule
  *Enterococcus faecalis* EF-2001 of present invention: 0.15 mg
  Glucose: 200 mg
  Starch: 600 mg
  The ingredients were mixed together, then 100 mg of 30% ethanol was added thereto, the mixture was dried at 60° C. to form granules, and then the granules were filled in a pouch.

<Preparation Example 2> Preparation of Health Food Containing *Enterococcus faecalis* EF-2001 of Present Invention as Active Ingredient

*Enterococcus faecalis* EF-2001 of present invention: 1 mg
Proper Amount of Vitamin Mixture
  Vitamin A acetate: 70 μg
  Vitamin E: 1.0 mg
  Vitamin: 0.13 mg
  Vitamin B2: 0.15 mg
  Vitamin B6: 0.5 mg
  Vitamin B12: 0.2 μg
  Vitamin C: 10 mg
  Biotin: 10 μg
  Nicotinamide: 1.7 mg
  Folic acid: 50 mg
  Calcium pantothenate: 0.5 mg Proper Amount of Inorganic Mixture
 Ferrous sulfate: 1.75 mg
 Zinc oxide: 0.82 mg
 Magnesium carbonate: 25.3 mg
 Potassium phosphate monobasic: 15 mg
 Calcium phosphate dibasic: 55 mg
 Potassium citrate: 90 mg
 Calcium carbonate: 100 mg
 Magnesium chloride: 24.8 mg The vitamin and mineral mixtures were prepared by mixing ingredients relatively suitable for health food at composition ratios preferred as embodiments, but the mixing ratios may be arbitrarily modified. The ingredients may be mixed together according to a conventional method for preparing health food, then the mixture may be prepared into granules, and the granules may be used to prepare a health food composition according to a conventional method.

<Preparation Example 3> Preparation of Health Beverage Containing *Enterococcus faecalis* EF-2001 of Present Invention as Active Ingredient

*Enterococcus faecalis* EF-2001 of present invention: 1 mg
Citric acid: 1000 mg
Oligosaccharide: 100 g
Plum concentrate: 2 g
Taurine: 1 g
Whole amount after addition of purified water: 900 ml The ingredients were mixed together according to a conventional method for preparing health beverage, then the mixture was stirred and heated at 85° C. for about 1 hour, and then the resulting solution was filtered, collected in a sterilized container, sealed, sterilized, refrigerated, and then used to prepare a health beverage composition.

The ingredients relatively suitable for favorite beverages were mixed at a composition ratio preferred as an embodiment, but the mixing ratio may be arbitrarily modified according to the local or national preference such as the consumed class, the consumed country, and the purpose of use.

<Preparation Example 4> Preparation of External Preparation Containing *Enterococcus faecalis* EF-2001 of Present Invention as Active Ingredient <4-1> Preparation of Ointment An ointment containing *Enterococcus faecalis* EF-2001 of the present invention was prepared by a conventional method according to the composition presented in [Table 1] below.

TABLE 1

| Ingredient | Content (%) |
| --- | --- |
| *Enterococcus faecalis* EF-2001 of present invention | 1.0 |
| Glycerin | 8.0 |
| Butylene glycol | 4.0 |
| Liquid paraffin | 15.0 |
| Beta-glucan | 7.0 |
| Carbomer | 0.1 |
| Caprylic/Capric triglycerides | 3.0 |
| Squalane | 1.0 |
| Cetearyl glucoside | 1.5 |
| Sorbitan stearate | 0.4 |
| Cetearyl alcohol | 1.0 |
| Beeswax | 4.0 |
| Preservative | Small amount |
| Fragrance | Small amount |
| Purified water | Remaining amount |
| Sum | 100 |

<Preparation Example 5> Preparation of Cosmetic Composition Containing *Enterococcus faecalis* EF-2001 of Present Invention as Active Ingredient <5-1> Nutrient Lotion Nutrient lotion containing *Enterococcus faecalis* EF-2001 of the present invention was prepared by a conventional method at the component ratio presented in [Table 2] below.

TABLE 2

| Ingredient | Content (wt %) |
| --- | --- |
| *Enterococcus faecalis* EF-2001 of present invention | 2.0 |
| Glyceryl stearate SE | 1.5 |
| Stearyl alcohol | 1.5 |
| Lanolin | 1.5 |
| Polysorbate 60 | 1.3 |
| Sorbitan stearate | 0.5 |
| Hydrogenated vegetable oil | 4.0 |
| Mineral oil | 5.0 |
| Trioctanoin | 2.0 |
| Dimethicone | 0.8 |
| Tocopherol acetate | 0.5 |
| Carboxyvinyl polymer | 0.12 |
| Glycerin | 5.0 |
| 1,3-Butylene glycol | 3.0 |
| Sodium hyaluronate | 5.0 |
| Triethanolamine | 0.12 |
| Uniside-oil 13 | 0.02 |
| Fragrance | Small amount |
| Distilled water | Remaining amount |
| Sum | 100 |

<5-2> Nourishing Cream

A nourishing cream containing *Enterococcus faecalis* EF-2001 of the present invention was prepared by a conventional method at the component ratio presented in [Table 3] below.

TABLE 3

| Ingredient | Content (wt %) |
| --- | --- |
| *Enterococcus faecalis* EF-2001 of present invention | 2.0 |
| Lipophilic monostearate glycerin | 1.5 |
| Cetearyl alcohol | 1.5 |
| Stearic acid | 1.0 |
| Polysorbate 60 | 1.5 |
| Sorbitan stearate | 0.6 |
| Isostearyl isostearate | 5.0 |
| Squalane | 5.0 |
| Mineral oil | 35.0 |
| Dimethicone | 0.5 |
| Hydroxyethylcellulose | 0.12 |
| Glycerin | 6.0 |
| Triethanolamine | 0.7 |
| Uniside-oil 13 | 0.02 |
| Fragrance | Small amount |
| Distilled water | Remaining amount |
| Sum | 100 |

INDUSTRIAL APPLICABILITY

In the present invention, it has been confirmed that *Enterococcus faecalis* EF-2001 exhibits the effect of inhibiting adipogenesis in adipocytes, and thus the *Enterococcus faecalis*, a culture solution thereof, or killed bacteria thereof can be greatly usefully used for the prevention, improvement and treatment of obesity that occurs through adipogenesis in adipocytes or obesity-induced metabolic syndrome disease.

The invention claimed is:

1. A method for inhibiting adipogenesis in adipocytes, the method comprising administering to a subject a pharmaceutically effective amount of killed bacteria of *Enterococcus faecalis* EF-2001.

2. The method according to claim 1, wherein the killed bacteria are killed by heat treatment.

3. The method according to claim 2, wherein the heat treatment is performed at a temperature of 60° C. to 140° C. for 1 to 40 minutes.

4. The method according to claim 1, wherein the killed bacteria are administered to the subject orally.

5. The method according to claim 1, wherein the killed bacteria are administered to the subject parenterally.

6. The method according to claim 1, wherein the killed bacteria are administered to the subject topically.

* * * * *